United States Patent [19]

McAdam et al.

[11] 4,168,220
[45] Sep. 18, 1979

[54] METHOD FOR DETECTING THE FOULING OF A MEMBRANE COVERED ELECTROCHEMICAL CELL

[75] Inventors: Will McAdam, Worcester; Robert M. Taylor, Lansdale, both of Pa.

[73] Assignee: Leeds & Northrup Company, North Wales, Pa.

[21] Appl. No.: 923,502

[22] Filed: Jul. 10, 1978

[51] Int. Cl.² .............................................. G01N 27/46
[52] U.S. Cl. .................................. 204/195 P; 204/1 T
[58] Field of Search ............................. 204/1 P, 195 P

[56] References Cited

U.S. PATENT DOCUMENTS

| | | | |
|---|---|---|---|
| 2,913,386 | 7/1959 | Clark | 204/195 P |
| 3,260,656 | 1/1966 | Ross | 204/1 P |
| 3,325,378 | 6/1967 | Greene et al. | 204/195 P |
| 3,661,748 | 5/1972 | Blackmer | 204/195 P |
| 3,663,409 | 5/1972 | Greene | 204/195 P |
| 3,718,568 | 2/1973 | Neuwelt | 204/195 P |
| 4,076,596 | 2/1978 | Connery et al. | 204/195 P |

Primary Examiner—T. Tung
Attorney, Agent, or Firm—William G. Miller, Jr.; Raymond F. MacKay

[57] ABSTRACT

In a polarographic cell of the type which avoids depletion of the species being measured in the sample, the fouling of the membrane covering of the cell is detected by utilizing an electrode which can be substituted for that electrode from which the species being measured is electrochemically generated. That electrode is spaced remotely from the closely spaced anode and cathode so that when it is substituted depletion of the species being measured occurs outside the membrane. By comparing the current output from the cell when it is operating in its normal mode with the output when it is operating with the substitute electrode, as by dividing one value by the other, the degree of fouling of the membrane covering the cell is determined.

6 Claims, 2 Drawing Figures

METHOD FOR DETECTING THE FOULING OF A MEMBRANE COVERED ELECTROCHEMICAL CELL

BACKGROUND OF THE INVENTION

This invention relates to electrochemical apparatus and more particularly to the improved polarographic type electrochemical cells for measuring the concentration of electrochemically active species in fluids. The invention is particularly concerned with a method for determining the degree of fouling of the membrane covering used on those electrochemical cells which operate in a manner to avoid the depletion of the species being measured in the sample in which the cell is immersed. Thus, the invention relates to a method for detecting the degree of membrane fouling in electrochemical cells of the type disclosed in U.S. Pat. No. 3,260,656 issued to J. W. Ross, Jr. on Jan. 12, 1966, and No. 4,076,596 issued to J. G. Connery, et al. on Feb. 28, 1978.

The description of the electrochemical cells of the type for which this method is useful is disclosed in U.S. Pat. No. 4,076,596 and is hereby incorporated by reference.

As set forth in the last mentioned U.S. patent, the basic polarographic apparatus as it was improved by Clark in a manner described in U.S. Pat. No. 2,913,386 is known as the Clark cell. The Clark cell utilizes a dual electrode structure immersed in an electrolyte and encased in a membrane which is permeable to the species to be measured, for instance, gaseous oxygen. Typically, when used for oxygen analysis the cathode in the Clark cell is formed of platinum or gold and is located closely adjacent to the membrane while the anode is formed of silver or lead, with an electrolyte usually made of an aqueous alkaline halide solution. In operation, the Clark cell is characterized by the fact that the cell consumes the species being measured and therefore causes a depletion of the species from the fluid sample in which the cell is immersed.

To avoid the disadvantages such as stirring dependencies, etc. which result from such a depletion of the sample, a cell structure of the type shown in the Ross U.S. Pat. No. 3,260,656 was proposed. That cell utilizes an electrode system which consumes the species being measured at one electrode and which generates a like quantity of the species at the electrode of opposite polarity, with those electrodes being closely spaced so as to avoid depletion of the species from the sample. The Ross type was further improved by the Connery et al cell structure of U.S. Pat. No. 4,076,596. For the purpose of this description, those cells which characteristically deplete the sample of the species being measured are referred to as Clark-type cells, or cells which operate in the Clark mode, whereas those cells such as the Ross or Connery et al cells are referred to generically as the Ross-type cells or cells operating in the Ross mode, in that they operate without depleting sample of the species being measured.

It will be evident that cells operating in the Clark mode will have current outputs which reduce as fouling of the membrane covering of the cell progresses, since the species being consumed by the cell is less able to pass throught the membrane whereas Ross-type cells have current outputs which will not change as a result of the fouling of the membrane since there is no requirement for the species to pass through the membrane to maintain a particular current output. Thus, as fouling progresses on the membrane of a Ross-type cell, the result is a decrease in the rate of response of the cell to changes in concentration of the species in the sample and observation of the output current of the cell provides no indication as to whether or not fouling is progressing. It is therefore an object of this invention to provide a method for determining the degree of fouling in a Ross-type cell.

SUMMARY OF THE INVENTION

A method is provided for determining the degree of fouling of a Ross-type cell while an electrochemically active species is being measured. The method comprises the steps of measuring the current output from the cell when the cell is operating in the Ross mode and then substituting an electrode other than the closely spaced anode and cathode so that electrode, which is remotely positioned from the anode and cathode, operates in place of either the anode or cathode to cause the cell to operate in the Clark mode. The current output of the cell is then measured with the cell operating in the Clark mode and a ratio is calculated between the two measurements, namely the Ross mode measurement and the Clark mode measurement to obtain a measure of the degree of fouling.

DESCRIPTION OF THE PREFERRED EMBODIMENTS

Figure 1:
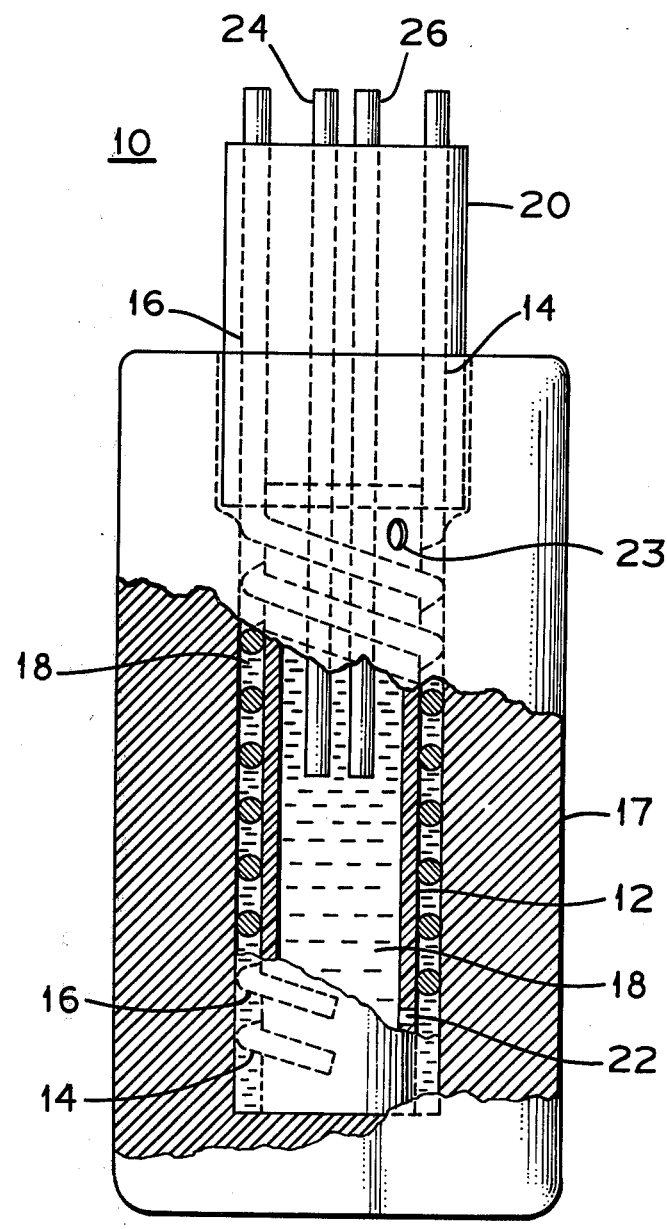
FIG. 1 is a diagram partially in cross section showing the construction of a Ross-type cell for which the invention can be utilized.

A Ross-type cell having a construction which follows the teaching of the Connery et al patent is shown in FIG. 1. The method of the invention is useful in determining the degree of fouling of the membrane of this cell as described below.

In FIG. 1, which is very similar to the construction of FIG. 7 of U.S. Pat. No. 4,076,596, there is shown an electrochemical cell 10 which comprises a hollow cylindrical base 12 of insulating material which has wound on its surface interleaved wire electrodes forming spirals about the base. These electrodes are shown as wires 14 and 16. The surfaces of these electrodes are exposed to the electrolyte 18 which is contained both in the internal portion of the cylindrical base as well as in that area between the electrodes exterior to the cylindrical base. The spacing between the electrodes 14 and 16 as they spiral around the base 12 is sufficiently close with respect to the thickness of the membrane 17 which covers the spiral winding that there will be no depletion of the species from the sample in which the cell is immersed, but instead the species will be generated at one electrode and consumed at the other electrode in a quantity dependent of the concentration of the species in the sample being measured.

The electrodes are brought out of the cell through a body portion 20 to which the membrane 17 is closely fitted so as to retain the electrolyte 18 in the spaces between the electrodes and in the interior portion of the base. There will be, of course, a thin film of electrolyte between the membrane 17 and the electrodes 14 and 16.

As shown in FIG. 1, two holes are provided in the base 12. They are shown as the lower hole or aperture 22, and the upper hole 23. These holes are provided so that the electrolyte interior to the base is in communication with the electrolyte exterior to the base.

As shown in FIG. 1, two additional electrodes, 24 and 26, enter through the body portion 20 directly into the interior of the cylindrical base 12 so that they are immersed in the electrolyte contained therein. One of these electrodes, such as 26, for example, may act as a substitute electrode in that it may be substituted for either the electrode 14 or the electrode 16, as will be further explained in the subsequent description.

Figure 2:
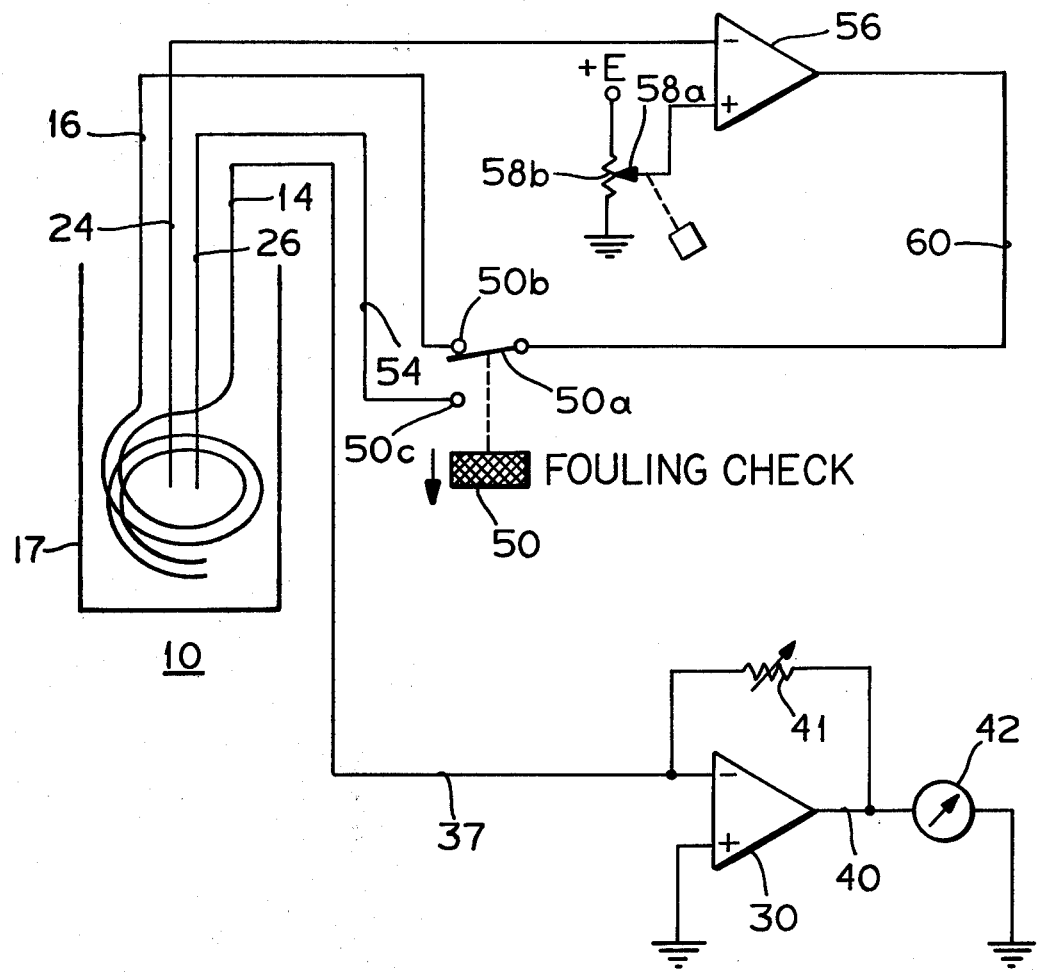
FIG. 2 is a circuit diagram showing the method for making the necessary measurements required by the novel method of the invention.

The novel method of this invention is shown in FIG. 2 wherein the Ross-type cell 10 of FIG. 1 is shown having a membrane 17 covering the spiral configuration formed by the electrode 14 and electrode 16 in the electrolyte medium between the membrane and the base (not shown) with the addition of a reference electrode 24 and a substitute electrode 26.

The current measuring circuit for measuring the output of the cell 10 includes a differential amplifier 30 which has its inverting input connected to line 37 and includes an adjustable feed-back resistor 41. The non-inverting input of amplifier 30 is, as shown, connected to ground so that the output on line 40 to voltmeter 42 indicates the current from electrode 14.

The desired predetermined bias of electrode 14 with respect to the reference electrode 24 is provided by amplifier 56 which has its non-inverting input connected to the movable contact 58a on slidewire 58b so as to provide a predetermined potential at the non-inverting input of amplifier 56. The slidewire 58b has one end connected to a potential source +E with the other end connected to ground. The adjustable contact 58a will normally be adjusted so that the potential of the non-inverting input to amplifier 56 will be that potential which is desired between the electrode 14 and reference electrode 24.

As shown in FIG. 2, the output of the amplifier 56 which acts as a power source is normally connected by way of line 60, switch contact 50a and contact 50b to the electrode 16 to maintain the current between electrode 16 and 14 at the value required to maintain the potential between electrodes 24 and 14 at a value equal to that potential tapped off a contact 58a.

When it is desired to check for membrane fouling of the cell 10, the switch 50 is actuated so that the movable contact 50a is brought into contact with contact 50c to connect line 60 to the substitute electrode 26 by way of line 54.

If, for example, it is assumed that the electrochemical cell 10 is being utilized to measure oxygen in the sample in which it is immersed, the electrode 16 serves at the anode while the electrode 14 serves as the cathode, and under normal operation the switch 50 is in the position shown with the reading on the voltmeter 42 indicating the concentration of oxygen by measuring the voltage drop across resistor 41 and hence the current output from the cell when it is operating in the Ross mode. The Ross mode is, of course, the mode in which the cell 10 operates when the switch 50 is in the position shown. The substitute electrode 26 which is remotely spaced from that electrode from which the species being measured is electrochemically generable, namely the anode 16 where oxygen is the species, is connected into the measuring circuit by the actuation of switch 50 which causes the cell 10 to operate in the Clark mode. In other words, with the contact 50a in contact with contact 50c, the reading on voltmeter 42 is a measurement of the current output from the cell with the cell in the Clark mode.

In order to determine the degree of the fouling of the membrane cover of the cell 10, it is necessary to compare the measurements made with the switch 50 in its two positions or, in other words, to compare the current output of the cell 10 as obtained when it is operating in the Ross mode with that obtained when it is operated in the Clark mode. This comparison may advantageously be made by dividing one reading by the other. For example, the current reading obtained during operation in the Ross mode may be divided by the current obtained with the cell being operated in the Clark mode. In each case for the particular cell configuration, that ratio will usually be somewhere between 5 and 10 for a typical design, when the membrane is unfouled. As membrane fouling increases, succeeding determinations of the Clark mode current will show an increase of the above mentioned ratio and the amount of increase of that ratio may be used as a measure of the degree of fouling of the membrane surface of the cell 10 and hence of the response of the electrode when it operates in the Ross mode. If it is preferred, of course, the ratio may be inverted and an opposite effect will be noted with the increase in fouling. By operating the switch 50 to make the fouling check when the cell 10 is immersed in the sample being measured, it will be evident that the conditions of temperature and sample concentration will be substantially the same unless, of course, the measurement is attempted at a time when those conditions are varying.

Where cell 10 is to be used for measuring chlorine, bromine, or iodine, the switch 50 substitutes electrode 26 for the anode 16. However, where it is desired to measure hydrogen, for example, the roles of electrodes 14 and 16 are interchanged and operation of switch 50 substitutes electrode 26 for the cathode.

It will be evident to those skilled in the art that the method of the invention can be utilized in a cell which does not have a reference electrode for it is only necessary to have a substitute electrode which can be substituted for either the anode or cathode so as to make a Clark type cell out of a Ross type cell.

The material for constructing the cell of FIG. 1 may be those specified in the Connery et al patent. For example, when measuring oxygen the anode and the substitute electrode may be platinum, the cathode may be silver and the reference electrode may be cadmium. The membrane 17 may be a silicone rubber and the electrolyte may be KOH. Variation of the materials are, of course, possible as long as attention is paid to the requisites for good operation.

What is claimed is:

1. A method for determining the degree of membrane fouling of a Ross-type cell being used to measure the concentration of an electrochemically active species in a fluid when said cell includes, in close-spaced relationship, a first electrode at which the species is electrochemically consumed, a second electrode at which the species is electrochemically generable, and another electrode positioned remotely from said first electrode but in the same electrolyte with said first and second electrodes, all electrodes being on the side of the membrane away from the fluid, comprising the steps of:

measuring the current output from said cell when said cell is operating in the Ross mode;

substituting said another electrode for said second electrode so as to cause said Ross-type cell to operate in the Clark mode;

measuring the current output from said cell when said Ross-type cell is operating in the Clark mode; and comparing said measurements to obtain an indication of the degree of fouling.

2. The method of claim 1 in which said comparison is made by dividing one measurement by the other.

3. A method for determining the degree of membrane fouling of an electrode assembly for measuring the concentration of a specific electrochemically active species in a fluid wherein the electrode assembly includes:

an electrolytic medium;

first electrode means of a material electrochemically inert to both said electrolyte and said species and in contact with said medium;

a membrane for separating said medium from said fluid, said membrane being selectively permeable to said species and in contact with said medium;

an electrical power source connected for biasing said first electrode means at a potential at which said species in said medium will be consumed at said first electrode means;

second electrode means of a material electrochemically inert to both said medium and said species, said second electrode means being in contact with said medium and connected to said power source for completing a circuit in which a current from said source can flow through both said electrode means at a level which is a function of such consumption;

said medium being one from which substantially only said species is electrolytically generable at said second electrode means at said current level, said second electrode means being biased by said power source at a potential at which said species in generable from said medium; and said first electrode means being so positioned with respect to second electrode means and said membrane that said species as generated at said second electrode means is available for consumption at said first electrode means in quantity dependent upon a tendency of said species to establish an equilibrium condition across said membrane between the concentration of said species respectively in said electrolyte and in said fluid; and third electrode means of a material electrochemically inert in both said medium and said species and positioned in said medium remotely from said first electrode so that when said species is generated by said third electrode it is not available for consumption by said first electrode; comprising the steps of:

measuring the current through said first and second electrode means;

substituting said third electrode for said second electrode in said circuit;

measuring the current through said first and third electrode means; and comparing the current through said first and second electrode means with the current through said first and third electrode means to obtain an indication of the degree of fouling.

4. A method for determining the degree of membrane fouling of an electrode assembly for measuring the concentration of a specific electrochemically active species in a fluid wherein the electrode assembly includes:

an electrolytic medium;

first and second electrode means of a material electrochemically inert to both said electrolyte and said species and in contact with said medium;

third and fourth electrode means positioned in said medium remotely from said first electrode so that any species generated by said third electrode is not available for consumption by said first electrode;

a membrane for separating said medium from said fluid, said membrane being selectively permeable to said species; and in contact with said medium;

an electrical power source connected so as to maintain the current flow between the first and second electrodes at a value such that the potential of the first electrode means with respect to the fourth electrode is maintained equal to a predetermined value such that said species in said medium will be consumed at said first electrode means and said current will be at a level which is a function of said consumption;

said medium being one from which substantially only said species is electrolytically generable at said second electrode means at said current level; and said first electrode means being so positioned with respect to said second electrode means and said membrane that said species as generated at said second electrode means is available for consumption at said first electrode means in quantity dependent upon a tendency of said species to establish an equilibrium condition across said membrane between the concentration of said species respectively in said medium and in said fluid; comprising the steps of:

measuring the current through said first and second electrode means;

substituting said third electrode for said second electrode in said circuit;

measuring the current through said first and third electrode means; and comparing the current through said first and second electrode means with said current through said first and third electrode means to obtain an indication of the degree of fouling.

5. A method for determining the degree of membrane fouling of an electrode assembly for measuring the concentration of a specific electrochemically active species in a fluid wherein the electrode assembly includes:

an electrolytic medium from which only said species is electrolytically generable;

a membrane selectively permeable to said species;

first and second electrode means of material electrochemically inert to both said medium and said species and having surfaces in contact with said medium;

means for supporting said first and second electrode means to position their respective surfaces in contact with said medium in an interleaved side by side relationship with said surfaces equidistant from said membrane and positioned so that the species generated at the surfaces of said second electrode is consumed at the adjacent surfaces of said first electrode without any substantial transfer of said species across the interface between said membrane and said fluid, and means connecting said first and second electrodes to a power source operable to bias said first and second electrodes at potentials to produce a current between said electrodes such that said species will be generated at said second electrode and consumed at said first electrode in quantity dependent upon the tendency of said species to establish an equilibrium condition across said membrane between the respective concentrations of said species in said medium and said fluid; and third electrode means positioned in said medium remotely from said first electrode so that any of said species generated at said third electrode is not available for consumption at said first electrode; comprising the steps of:

measuring the current through said first and second electrode means;

substituting said third electrode for said second electrode in said circuit;

measuring the current through said first and third electrode means; and comparing the current through said first and second electrode means with said current through said first and third electrode means to obtain an indication of the degree of fouling.

6. The method as set forth in claim 5 in which said comparison is made by dividing one measurement by the other.

* * * * *